United States Patent [19]

Ginos et al.

[11] Patent Number: 4,608,391

[45] Date of Patent: Aug. 26, 1986

[54] CATECHOLAMINE DERIVATIVES, A PROCESS FOR THEIR PREPARATION AND PHARMACEUTICAL COMPOSITIONS THEREOF

[75] Inventors: James Z. Ginos; George C. Cotzias, both of New York, N.Y.

[73] Assignee: Cornell Research Foundation Inc., Ithaca, N.Y.

[21] Appl. No.: 30,578

[22] Filed: Apr. 16, 1979

Related U.S. Application Data

[60] Division of Ser. No. 812,854, Jul. 5, 1977, Pat. No. 4,181,738, which is a continuation of Ser. No. 746,026, Nov. 30, 1976, abandoned.

[51] Int. Cl.⁴ .................... A61K 31/135; C07C 91/32
[52] U.S. Cl. .................... 514/654; 514/554; 564/142; 564/170; 564/280; 564/374; 260/501.18
[58] Field of Search ................ 260/570.8 R; 424/316, 424/330; 564/374; 514/654

[56] References Cited

U.S. PATENT DOCUMENTS

| | | | |
|---|---|---|---|
| 2,006,114 | 6/1935 | Rosenmund et al. | 260/570.8 |
| 2,276,618 | 3/1942 | Kulz | 260/570.8 |
| 2,597,247 | 5/1952 | Kerwin et al. | 260/570.8 X |
| 2,597,248 | 5/1952 | Kerwin et al. | 260/570.8 |
| 4,175,136 | 11/1979 | Nedeler et al. | 260/570.8 X |

*Primary Examiner*—Robert V. Hines
*Attorney, Agent, or Firm*—Schwartz, Jeffery, Schwaab, Mack, Blumenthal & Evans

[57] ABSTRACT

New dopamine derivatives are disclosed, which are tertiary amines and which exhibit especially dopaminergic properties, and which have the formula

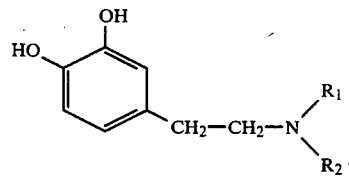

wherein $R_1$ signifies an alkyl group containing at least 4 carbon atoms, a cycloalkyl alkyl group, a cycloalkyl group or a phenylalkyl group and $R_2$ signifies an alkyl group, a cycloalkyl alkyl group, a cycloalkyl group, or a phenylalkyl group.

49 Claims, No Drawings

CATECHOLAMINE DERIVATIVES, A PROCESS FOR THEIR PREPARATION AND PHARMACEUTICAL COMPOSITIONS THEREOF

This is a division of application Ser. No. 812,854, filed July 5, 1977 and now U.S. Pat. No. 4,181,738, which is a continuation of application Ser. No. 746,026, filed Nov. 30, 1976, now abandoned.

BACKGROUND OF THE INVENTION

The invention relates to new catecholamine derivatives.

Catecholamine derivatives like adrenaline, noradrenaline, dopamine and others are present in various parts of the human body and are known to have neurotransmitter functions in various parts of the nervous system, inter alia, in the brain. Many pharmacologically active substances, which are chemically related to the biogenic catecholamines and in which some of the pharmacological effects of such biogenic amines are enhanced, have been designed in order to influence adverse health conditions that are caused by any disorder in the body household of biogenic amines; among these are primarily sympathomimetic substances which influence the circular vascular system.

But there are only very limited possibilities for influencing diseases which are connected with deficiencies of such biogenic amines in the brain, like e.g. the Parkinson's disease, since catecholamine derivatives do not easily cross the so-called blood-brain barrier. Another disadvantage of such compounds is the fact that they are easily inactivated by enzymatic reactions in the intestinal tract and/or the liver and therefore are not suited for oral administration.

SUMMARY OF THE INVENTION

It is an object of the present invention to provide new pharmacologically active catecholamine derivatives with dopaminergic properties, especially compounds which exhibit selective dopaminergic properties and reduced cholinergic side effects and are low in toxicity. It is a further object of this invention to provide such compounds which show increased ability in crossing the blood-brain barrier.

It is a further object to provide such compounds which show increased resistance against enzymatic inactivation after oral administration.

It is a further object of this invention to provide pharmacologically active compounds which are effective in ameliorating physical or physiological and behavioral health disorders which are connected with a disturbed dopamine metabolism or dopamine deficiencies, particularly disturbance of the dopamine household in the brain. Furthermore, it is an object of this invention to provide such compounds which show an increased resistance to deamination by monoamine oxidase (MAO).

It is a special object of this invention to provide new compounds which are effective against Parkinson's disease, especially compounds which are effective in ameliorating the symptoms of Parkinson's disease while at the same time avoiding the pharmacological side effects of L-Dopa (1-3,4-dihydroxyphenylalanine).

It is a further object of this invention to provide new compounds which are able to compensate dopamine deficiency and thereby are effective to prevent conditions which are favorable for the forming and/or growing of malignant tumor cells.

It is a further object of this invention to provide a process for the production of tertiary 3,4-dihydroxyphenethylamines.

It is still another object of this invention to provide pharmaceutical solid or liquid formulations for enteral, especially oral applications containing tertiary 3,4-dihydroxyphenethylamines.

It is another object of this invention to provide pharmaceutical formulations for parenteral administration, e.g. injection, containing tertiary 3,4-dihydroxyphenethylamines.

It is a further object of this invention to provide a method for treatment or prevention of physical or physiological and behavioral health disorders, which are caused by or connected with disturbances of the dopamine household in a human body, e.g., by a disturbed dopamine metabolism or dopamine deficiencies.

It is a further object of this invention to provide a method for treatment or prevention of physical or physiological and behavioral health disorders, which are caused by disturbances of the dopamine household in the brain of a human body. It is a special object of this invention to provide a method of treatment of Parkinson's disease.

In order to accomplish the foregoing objects according to the present invention there are provided new compounds of the formula I.

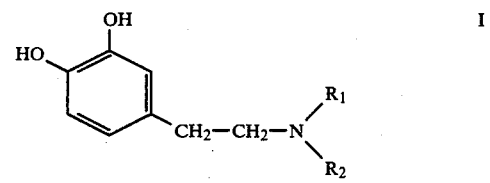

wherein
R$_1$ signifies an alkyl group containing at least 4 carbon atoms, a cycloalkyl alkyl group, a cycloalkyl group or a phenylalkyl group, and R$_2$ signifies an alkyl group, a cycloalkyl alkyl group, a cycloalkyl group or a phenylalkyl group, and their pharmacologically acceptable salts.

The substituents R$_1$ and R$_2$ together preferably contain 24 or less carbon atoms, most preferably between 5 and 20 especially between 7 and 12 carbon atoms. Typically at least one of the substituents R$_1$ and R$_2$ is an alkyl group.

If R$_1$ and/or R$_2$ represent alkyl groups, these groups may be straight or branched and preferably are primary alkyl groups. They may contain up to 20 carbon atoms preferably not more than 12 carbon atoms, e.g., n-propyl, n-butyl, isobutyl, n-pentyl or a branched primary pentyl group a straight or a primary branched hexyl-, heptyl-, octyl-, nonyl-, decyl-, undecyl- or a dodecyl group.

If both R$_1$ and R$_2$ represent alkyl groups, it is preferred that they are different from each other and/or that R$_2$ comprises at least 2 carbon atoms. Preferably at least one of the alkyl groups contains a chain of at least 3, most preferably at least 5 carbon atoms.

If R$_1$ and/or R$_2$ represent cycloalkyl alkyl groups, they may contain 4 to 20, preferably 4 to 12 carbon atoms. The cycloalkyl ring may contain 3 to 8 preferably 3 to 6 carbon atoms and may be substituted by lower alkyl groups. The alkylene chain to which the cycloalkyl ring is substituted preferably is a primary alkylene group and preferably includes a chain of 1 to 6, preferably 1 to 3 carbon atoms. Suitable cycloalkylalkyl groups are cyclopropylmethyl, 2-cyclohexylethyl, 3-cyclohexyl-n-propyl or the like.

If $R_1$ and/or $R_2$ represent cycloalkyl groups their cycloalkyl ring may contain 3 to 15 preferably 5 to 7 carbon atoms and may be substituted by lower alkyl.

If $R_1$ and/or $R_2$ represent phenylalkyl groups, the alkylene chain on which the phenyl is substituted preferably is a primary alkylene group and preferably includes a chain of 1 to 6, especially 2 or 3 carbon atoms. The phenyl ring may be substituted by lower alkyl, lower alkoxy or halogen such as fluorine, chlorine or bromine. Suitable phenylalkyl groups are benzyl, phenylethyl, monochlorophenylethyl, trimethylphenylethyl, methoxyphenethyl, n-butylphenyl and the like.

According to the present invention, there is further provided a process for preparing the new compounds of formula I comprising the step of removing the protective groups X from a compound of formula II

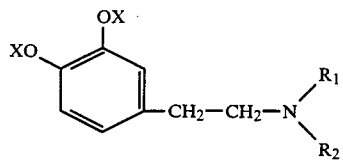

wherein $R_1$ and $R_2$ are as defined above and X represents a removable protective group.

According to the invention, there are further provided pharmaceutical compositions comprising the abovedescribed compounds of formula I or their pharmaceutically acceptable salts, and optionally an inert diluent.

Further objects, features and advantages of the present invention will become apparent from the detailed description of the invention which follows.

DETAILED DESCRIPTION OF THE INVENTION

The new compounds of formula I according to this invention and their pharmaceutically acceptable salts exhibit valuable pharmacological properties and therefore are useful in medical treatments. In particular, they are useful in the treatment of physical or physiological and behavioral health disorders which are caused by or connected with disturbances of the dopamine household in the human body, especially in the treatment of Parkinson's disease, since they exhibit dopaminergic properties. For example, in caudactomized mice, which had the right caudate nucleus partially ablated according to the method described by V. Lotti in Life Science, 10 781 (1971) three weeks before i.p. administration of 0.1 to 500 mg/kg body weight, these compounds cause a curving of the body toward the side with the lesion. The administered doses can vary considerably depending on the type of the compound, the animal, the mode of administration and the treated conditions. Usually good results are obtained with dosages between 0.1 and 500 mg/kg body weight. These doses can be administered enterally, preferably orally, or parenterally. For example, daily oral doses for larger mammals can be chosen between 50 and 600 mg These doses can be administered in form of partial doses of between 12 and 300 mg or as sustained release formulations.

According to a further feature of the invention, there are provided pharmaceutical compositions containing at least one of the compounds of formula I or their pharmaceutically acceptable salts. The compositions may take the form of solid or liquid formulations for enteral, preferably oral, or for parenteral administration. Thus the formulations may be in the form of capsules, tablets, coated tablets, suppositories, emulsions or solutions. These formulations may comprise conventional pharmaceutical carriers, e.g., solids, such as starch, lactose, mannit, polyvinyl pyrrolidene or liquids such as sterile water, pharmaceutically acceptable alcohols or fatty oils, and may further comprise pharmaceutical adjuvants, e.g., binders or lubricants for tabletting, stabilizing, flavoring or emulsifying agents.

According to the present invention, the new compounds of formula I may be obtained by removing the protective groups X from compounds of formula II by conventional methods.

The groups X may be chosen from any protective groups which are suitable for protecting phenolic hydroxy groups, e.g., by forming phenol ethers or esters, and which can be split off by hydrolysis, preferably acidic hydrolysis or by hydrogenolysis. Thus in compounds of formula II, X may represent lower alkyl, preferably methyl, or a benzyl group, or both substituents X together form a lower alkylene group, preferably a methylene group. The protective groups can be removed by conventional acidolytic methods for phenol ether splitting, e.g., by treating the compounds of formula II with Lewis acids or with concentrated hydrohalogenic acids. Protective groups X which may be split off by conventional hydrogenolysis comprise the benzyl group or substituted benzyl groups. The use of protective groups which can be eliminated by hydrogenolysis is advisable if the substituents $R_1$ and/or $R_2$ include radicals which are sensitive to strong acidic conditions such as lower cycloalkyl groups or methoxy phenyl alkyl groups. Hydrogenolysis of course cannot be applied to compounds wherein $R_1$ and/or $R_2$ represent benzyl. Preferably starting materials of formula II are used wherein X is methyl and the demethylation is performed by treatment with strong hydrohalogenic acids such as hydrobromic or hydroiodic acids, preferably according to the method described by Neumeyer el al. (Pharm. Sci. 59, 1850 (1970)).

The compounds of formula I are water soluble and can be recovered in free form or in form of a salt. A salt form can easily be transferred into the free form and vice versa. Acid addition salts of compounds of formula I can be formed with mineral acids such as hydrochloric, hydrobromic, hydroiodic or sulfuric acid or with organic acids such as fumaric acid. Phenolate salts of compounds of formula I can be formed with organic or inorganic bases such as sodium hydroxide.

The starting materials of formula II can be obtained in conventional manner, e.g., by reacting a compound of formula III

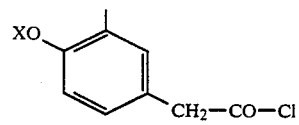

wherein X is as defined above, preferably 3,4-dimethoxyphenylacetyl chloride, with an amine of formula IV

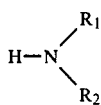

wherein $R_1$ and $R_2$ are as defined above and reducing the resulting phenylacetamide derivative. The reduction preferably is effected by treatment with diborane under anhydrous conditions.

Compounds of formula II can also be obtained by alkylating compounds of formula V

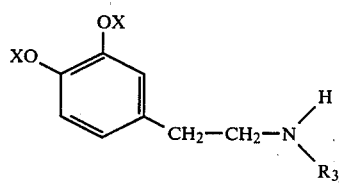

wherein X is as defined above and $R_3$ represents hydrogen or any of the substituents which are defined for $R_2$ above by conventional alkylating methods.

For example, compound of formula II wherein $R_1$ and $R_2$ are the same can be obtained by treating primary amines of formula V ($R_3$=H) with conventional alkylating agents such as alkylhalides, dialkylsulfates and the like. In order to obtain compounds of formula II wherein $R_1$ and $R_2$ are different, secondary amines of formula V are alkylated. For introducing methyl or cycloalkyl group so called reductive alkylation by reacting the amine of formula II with an excess of the appropriate aldehyde or ketone under hydrogenating conditions in the presence of a hydrogenation catalyst is preferred. For introducing other substituents the amines of formula II preferably are reacted with a corresponding acyl chloride and the resulting amides are subsequently reduced.

Compounds of formula V can be prepared by reacting a compound of formula III with the corresponding amine and reducing the resulting amides. Secondary amines of formula IV as well as secondary amines of formula V can be obtained by reacting a corresponding primary amine with an appropriate acyl chloride and reducing the corresponding amides.

The invention will now be further described by the following examples, which are intended to be illustrative only.

EXAMPLE 1

N-Methyl-N-n-butyl-β-(3,4-dihydroxyphenyl)ethylamine

A solution of 13.1 ml of 57% HI (hydro-iodic acid), 6.5 ml acetanhydride and 2.25 g (8.25 mmol) of N-methyl-N-n-butyl-β-(3,4-dimethoxy phenyl)ethylamine hydrochloride was refluxed for 0.75 hr. under nitrogen and then the solvent was removed under reduced pressure. The viscous residue was redissolved in 7 ml of absolute ethanol and evaporated again under high vacuum. The pale yellow residue was redissolved in 7 ml of absolute ethanol diluted with 25 ml of ethylacetate, and induced to crystallize by scratching. The crystalline product was filtered off, dissolved in 30 ml of water, and basified with sodium-hydrogen carbonate, and the free amine was extracted exhaustively with ethyl acetate. The solid residue obtained after removal of the solvent was dissolved in 8 ml of absolute ethanol and treated with hydrochlorine acid-saturated absolute ether. This yielded a colorless viscous oil as a precipitate, which was centrifuged off and triturated with ether until it changed into a sticky solid. This was recrystallized from 5 ml of warm ethanol diluted with 65 ml of ethylacetate.

The resulting N-methyl-N-n-butyl-β-(3,4-dihydroxyphenyl)ethylamine-hydrochloride exhibited a melting point of 146° to 148° C.

Preparation of the starting material:

(1a)

N-Methyl-N-n-butyl-β-(3,4-dimethoxyphenyl)acetamide

To a solution of 35 ml of chloroform and 11.24 g (0.19 m) of N-methyl-N-n-butylamine was added dropwise with agitation a solution of 35 ml of chloroform and 13.6 g (0.063 mol) of 3,4-dimethoxy-phenylacetyl chloride at 0°. The reaction was completed after 1 hr of heating at 50°-55°. The chloroform solution was washed successively with 0.1N hydrochloric acid 10% aqueous sodium hydroxide and water. The organic layer, after drying over anhydrous magnesium sulfate, yielded upon removal of the solvent the crude N-methyl-N-n-butyl-β-(3,4-dimethoxyphenyl)acetamide, a yellow oil. This was purified by high vacuum distillation and was used in the next synthetic step.

(1b)

N-Methyl-N-n-butyl-β-(3,4-dimethoxyphenyl)ethylamine Hydrochloride

A solution of 150 ml of tetrahydrofuran (THF) and 14.0 g (0.0557 mol) of the above compound was stirred slowly into 99.7 ml (0.95M) of diborane at −5° to 0° under anhydrous conditions and under a nitrogen atmosphere over a period of 15-20 min. The temperature was allowed to rise to 20° C. After refluxing for 0.75 hr, the reaction was complete. After cooling to room temperature, 6.0N hydrochloric acid (25 ml) was added carefully to the reaction solution because of the considerable foaming caused by the evolution of $H_2$. The total volume was reduced to about 40 ml by distillation at atmospheric pressure. The remaining aqueous phase was diluted with 40 ml of water, basified with 50% aqueous sodium hydroxide, and extracted with ether (4×50 ml). The ether extracts were combined, washed with water to a neutral pH, dried over anhydrous magnesium sulfate and filtered. The ether was reduced in volume to 50 ml and treated with hydrochloric acid saturated anhydrous ether. The oily precipitate crystallized out slowly under refrigeration to a white solid which was filtered, washed with ether, and dried to a constant weight. An IR (film) and a $^1$H NMR scanning of the colorless viscous oil remaining after evaporation of the mother liquor indicated that most of it consisted of the amine complexed with diborane. This was dissolved in 10 ml of tetrahydrofurane and refluxed with aqueous 6N hydrochloric acid, and the above extractive procedure was repeated, yielding an additional portion of the N-methyl-N-n-butyl-β-(3,4-dimethoxyphenyl)ethylamine hydrochloride. The two crops were combined and recrystallized from $CH_3OH$-ether; mp 130.5°-131°.

Analogous to Example 1 the following compounds of formula I are obtained by splitting off the protective groups X from corresponding compounds of formula II:

| Example No. | R₁ | R₂ | | mp. |
|---|---|---|---|---|
| 2 | phenethyl | phenethyl | | |
| 3 | n-propyl | n-butyl | HCl*: | 136–138° C. |
| 4 | n-pentyl | methyl | HCl*: | 71–73° C. |
| 5 | n-propyl | n-pentyl | HI**: | 112–113° C. |
| 6 | n-pentyl | n-pentyl | HCl*: | 90–91° C. |
| 7 | isobutyl | methyl | HCl*: | 135–136° C. |
| 8 | n-propyl | isobutyl | HCl*: | 94–96° C. |
| 9 | n-propyl | sec.butyl | | 100–101° C. |
| 10 | sec.butyl | sec.butyl | HCl*: | 125–127° C. |
| 11 | n-propyl | phenethyl | HCl*: | 50–55° C. |
| 12 | phenethyl | methyl | HCl*: | 80–85° C. |
| 13 | n-butyl | n-butyl | HCl*: | 108–109° C. |

*HCl = Hydrochloride
**HI = Hydroiodide

Analogous to example 1 are further prepared the following compounds of formula I by splitting off the protective groups X from corresponding compounds of formula II.

| R₁ | R₂ |
|---|---|
| myristyl | n-propyl |
| 4-octyldodecyl | n-butyl |
| lauryl | n-octyl |
| n-hexadecyl | methyl |
| n-heptyl | n-pentyl |
| n-octadecyl | methyl |
| cyclopropylmethyl | n-pentyl |
| cyclohexylethyl | methyl |
| cyclooctylethyl | methyl |
| 5-(4-methylcyclohexyl)pentyl | ethyl |
| cyclopentadecylmethyl | methyl |
| cyclohexylethyl | methyl |
| cyclopropyl | n-pentyl |
| 3-methyl-2-isopropylcyclohexyl | methyl |
| cycloheptyl | methyl |
| cyclodlodecyl | methyl |
| 2-methylcyclopentadecyl | methyl |
| cyclohexyl | cyclohexyl |
| m-methylphenethyl | methyl |
| o-chlorophenethyl | methyl |
| p-methoxyphenethyl | methyl |
| 4-(4-fluorophenyl)butyl | methyl |
| 10-(2-isopropyl- -methylphenyl)decyl | methyl |

EXAMPLE 15

Capsules for oral application 1.0 kg of N-n-propyl-N-n-butyl-β-(3,4-dihydroxyphenyl ethylamine, hydrochloride and 1.0 kg of mannite are thoroughly mixed and the mixture is filled into gelatine capsules in portions of 100 mg per capsule.

EXAMPLE 16

2 capsules which are prepared according to Example 15 are administered to an adult person 6 times per day for the treatment of Parkinson's disease.

The compounds of formula I or their pharmacologically acceptable salts are useful in the treatment of hypotensive states especially hypotensive or shock-like states resulting from cardiac infarctions or liver damage. For example good results are obtained by administering 2–5 mp/minutes/ml infusion to larger mammals.

What is claimed is:

1. A method of treatment of physical or physiological and behavioural health disorders, which are caused by or connected with disturbances of the dopamine household in mammals comprising the step of administering to a mammal 0.1 to 500 mg/kg of a compound of the formula

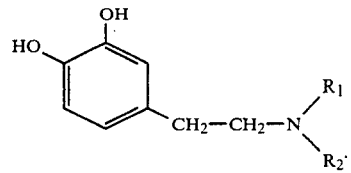

wherein
R₁ signifies a phenylalkyl group and
R₂ signifies an alkyl group, a cycloalkylalkyl group, a cycloalkyl group, or a phenylalkyl group, and the pharmaceutically acceptable salts thereof.

2. The method as defined in claim 1, wherein
R₁ signifies a phenylalkyl group, which is unsubstituted or substituted by lower alkyl, lower alkoxy, or halogen, containing 7 to 20 carbon atoms, and
R₂ signifies an alkyl group containing 1 to 20 carbon atoms, an unsubstituted or lower alkyl-substituted cycloalkylalkyl group containing 4 to 20 carbon atoms, an unsubstituted or lower alkyl-substituted containing 3 to 20 carbon atoms or a phenylalkyl group which is unsubstituted or substituted by lower alkyl, lower alkoxy, or halogen containing 7 to 20 carbon atoms.

3. The method as defined in claim 2, wherein R₁ and R₂ together contain 24 or less carbon atoms.

4. The method as defined in claim 3, wherein R₁ and R₂ each contain 12 or less carbon atoms.

5. The compound as defined in claim 2, wherein R₂ signifies alkyl containing 1 to 20 carbon atoms.

6. The method as defined in claim 2, wherein R₁ is phenethyl and R₂ is phenethyl or alkyl.

7. The method as defined in claim 5, wherein R₂ is alkyl selected from the group consisting of n-propyl, n-butyl, isobutyl, primary pentyl, primary hexyl, primary heptyl, primary octyl, primary nonyl, primary decyl, primary undecyl, and primary dodecyl.

8. The method as defined in claim 2, wherein the phenylalkyl group comprises a primary alkylene containing 1 to 6 carbon atoms.

9. The method as defined in claim 8, wherein the alkylene contains 2 to 3 carbon atoms.

10. The method as defined in claim 2, wherein the phenyl alkyl group is selected from the group consisting of benzyl, phenethyl, monochlorophenethyl, trimethylphenethyl, methoxyphenethyl, and n-butylphenethyl.

11. The method as defined in claim 2, wherein R₁ is m-methylphenethyl and R₂ is methyl.

12. The method of treatment as defined by claim 1, wherein the administering step comprises administering to a larger mammal being from about 0.5 to 10 mg/kg of said compound.

13. A method of treatment as defined by claim 12, wherein the administering step comprises administering a daily dosage of from about 50 to 600 mg of said compound.

14. The method of treatment as defined by claim 13, wherein said administering step comprises oral administration of said daily dosage.

15. The method as defined in claim 1 which is a method of treating Parkinson's disease, comprising the step of administering to a human being a daily dosage of from about 50 to 600 mg of a compound.

16. The method of treating Parkinson's disease as defined by claim 15, wherein said administering step comprises oral administration of said daily dosage.

17. The method of treating Parkinson's disease as defined by claim 15, comprising the step of administering to a human being a daily dosage of from about 50 to 600 mg of a compound of formula

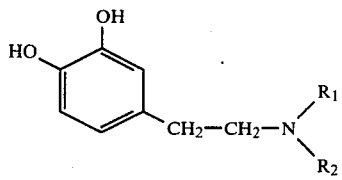

wherein
$R_1$ signifies a phenyl alkyl group which may be substituted by lower alkyl, lower alkoxy, or halogen, and $R_2$ is alkyl selected from the group consisting of n-propyl, n-butyl, isobutyl, primary pentyl, primary hexyl, primary heptyl, primary octyl, primary nonyl, primary decyl, primary undecyl, and primary dodecyl.

18. A compound of the formula

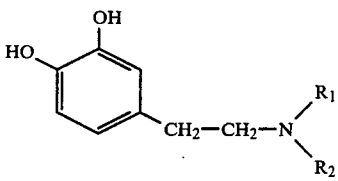

wherein $R_1$ and $R_2$ each are phenethyl, $R_1$ is phenethyl and $R_2$ is n-propyl, $R_1$ is o-chlorophenethyl and $R_2$ is methyl, $R_1$ is 4-(4-flourophenyl)butyl and $R_2$ is methyl, or $R_1$ is 10-(2-isopropylmethylphenyl)decyl and $R_2$ is methyl, and the pharmaceutically acceptable salts thereof.

19. The compound as defined in claim 18, wherein $R_1$ and $R_2$ are each phenethyl.

20. The compound as defined in claim 18, wherein $R_1$ is phenethyl and $R_2$ is n-propyl.

21. The compound as defined in claim 18, wherein $R_1$ is o-chlorophenethyl and $R_2$ is methyl.

22. The compound as defined in claim 18, wherein $R_1$ is 4-(4-fluorophenyl)butyl and $R_2$ is methyl.

23. The compound as defined in claim 18, wherein $R_1$ is 10-(2-isopropylmethylphenyl)decyl and $R_2$ is methyl.

24. A pharmaceutical composition comprising at least one compound as defined by claim 18 and a pharmaceutically acceptable diluent.

25. A pharmaceutical composition comprising at least one compound as defined by claim 19 and a pharmaceutically acceptable diluent.

26. A pharmaceutical composition comprising at least one compound as defined by claim 20 and a pharmaceutically acceptable diluent.

27. A pharmaceutical composition comprising at least one compound as defined by claim 21 and pharmaceutically acceptable diluent.

28. A pharmaceutical composition comprising at least one compound as defined by claim 22 and a pharmaceutically acceptable diluent.

29. A pharmaceutical composition comprising at least one compound as defined by claim 22 and a pharmaceutically acceptable diluent.

30. A method of treatment of physical or physiological and behavioral health disorders, which are caused by or connected with disturbances of the dopamine household in mammals comprising the step of administering to a mammal 0.1 to 500 mg/kg of a compound of the formula

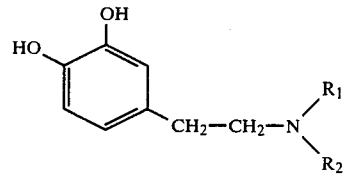

wherein $R_1$ and $R_2$ each are phenethyl, $R_1$ is phenethyl and $R_2$ is n-propyl, $R_1$ is o-chlorophenethyl and $R_2$ is methyl, $R_1$ is 4-(4-flourophenyl)butyl and $R_2$ is methyl, or $R_1$ is 10-(2-isopropylmethylphenyl)decyl and $R_2$ is methyl, and the pharmaceutically acceptable salts thereof.

31. The method as defined in claim 30, wherein $R_1$ and $R_2$ each are phenethyl.

32. The method as defined in claim 30, wherein $R_1$ is phenethyl and $R_2$ is n-propyl.

33. The method as defined in claim 30, wherein $R_1$ is o-chlorophenethyl and $R_2$ is methyl.

34. The method as defined in claim 30, wherein $R_1$ is 4-(4-fluorophenyl)butyl and $R_2$ is methyl.

35. The method as defined in claim 30, wherein $R_1$ is 10-(2-isopropylmethylphenyl)decyl and $R_2$ is methyl.

36. The method of treatment as defined by claim 30, wherein the administering step comprises administering to a larger mammal being from about 0.5 to 10 mg/kg of said compound.

37. A method of treatment as defined by claim 36, wherein said administering step comprises administering a daily dosage of from about 50 to 600 mg of said compound.

38. A method of treatment as defined by claim 37, wherein said administering step comprises oral administration of said daily dosage.

39. A method as defined in claim 30 which is a method of treating Parkinson's disease, comprising the step of administering to a human being a daily dosage of from about 50 to 600 mg of said compound.

40. The method of treating Parkinson's disease as defined by claim 39, wherein said administering step comprises oral administration of said daily dosage.

41. The method of treating Parkinson's disease as defined by claim 39, comprising the step of administering to a human being a daily dosage of from about 50 to 600 mg of a compound of formula

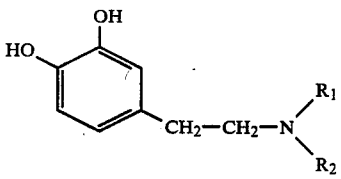

wherein $R_1$ and $R_2$ each are phenethyl, $R_1$ is phenethyl and $R_2$ is n-propyl, $R_1$ is o-chlorophenethyl and $R_2$ is methyl, $R_1$ is 4-(4-flourophenyl)butyl and $R_2$ is methyl, or $R_1$ is 10-(2-isopropylmethylphenyl)decyl and $R_2$ is methyl, and the pharmaceutically acceptable salts thereof.

42. The method as defined in claim 41, wherein $R_1$ is phenethyl and $R_2$ is n-propyl.

43. A compound of claim 20 which is the hydrochloride salt of N-phenethyl-N-propyl-3,4-dihydroxyphenethylamine.

44. A dopaminergic composition comprising a dopaminergically effective amount of at least one compound of claim 20 and an inert pharmaceutical carrier.

45. A composition of claim 44, wherein the compound is the hydrochloride salt of N-phenethyl-N-propyl-3,4-dihydroxyphenethylamine.

46. A method of inducing dopaminergic activity in warm-blooded animals comprising administering to warm-blooded animals a dopaminergically effective amount of at least one compound of claim 20.

47. The method of claim 46, wherein the compound is the hydrochloride salt of N-phenethyl-N-propyl-3,4-dihydroxyphenethylamine.

48. The method of claim 47, wherein the compound is orally administered.

49. The method as defined in claim 2, wherein $R_1$ is p-methoxyphenethyl and $R_2$ is methyl.

* * * * *

UNITED STATES PATENT AND TRADEMARK OFFICE
CERTIFICATE OF CORRECTION

PATENT NO. : 4,608,391
DATED : August 26, 1986
INVENTOR(S) : James Z. Ginos et al It is certified that error appears in the above—identified patent and that said Letters Patent is hereby corrected as shown below:

ol. 1, line 10, before "BACKGROUND OF THE INVENTION", should ead

--This invention was made with Government support under rant No. 11131 awarded by the Department of Health, Education nd Welfare. The Government has certain rights in the nvention.--

Signed and Sealed this

Eighth Day of September, 1987

Attest:

DONALD J. QUIGG

Attesting Officer

Commissioner of Patents and Trademarks